US00PP11224P

United States Patent [19]

Sherman

[11] Patent Number: Plant 11,224

[45] Date of Patent: Feb. 15, 2000

[54] PLUM TREE NAMED 'GULFBEAUTY'

[76] Inventor: Wayne B. Sherman, University of Florida, P.O. Box 110690, Gainesville, Fla. 32611-0609

[21] Appl. No.: 08/922,258

[22] Filed: Sep. 2, 1997

[51] Int. Cl.[7] ..... A01H 5/00

[52] U.S. Cl. ..... Plt./184

[58] Field of Search ..... Plt./38.1, 184

[56] References Cited

U.S. PATENT DOCUMENTS

P.P. 10,116 11/1997 Gerawan ..... Plt./38.1

*Primary Examiner*—Howard J. Locker
*Assistant Examiner*—Kent L. Bell

[57] ABSTRACT

A Japanese-type plum tree characterized by its low winter chilling adaptation to central and north Florida, early May ripening of dark red skin fruit and regular, high annual fruit production.

1 Drawing Sheet

BACKGROUND OF THE NEW VARIETY

The present invention relates to a new and distinct variety of plum tree which is named 'Gulfbeauty' and, more particularly to a plum tree which is adapted to central and north Florida winter climate with annual and heavy crops which ripen in the early May in the adapted area. Contrast is made to 'Gulfruby' plum with which it is cross fruitful. This new variety is a promising candidate for commercial success in that it bears fruit ripening in early season in Florida when few plums are available from the U.S.

ORIGIN OF THE VARIETY

The present invention relates to the discovery and asexual propagation of a new variety of Japanese type plum tree, *Prunus salicina,* originating from the University of Florida stonefruit breeding programs, which herein after will be denominated varietally as 'Gulfbeauty' plum tree. 'Gulfbeauty' originated from a $4^{th}$ generation polycross of Florida selections. The original cross, made in 1967, was from a bulk lot of hybrid seed from plum cultivars 'Ozark Premier', 'Burbank', 'Beauty', and 'Bruce' pollinated by Taiwan, all unpatented. 'Taiwan' resulted from a 1957 seed importation of 'Hung-ju' (unpatented) open pollinated in Taiwan. The present variety was selected as the first plum selection in 1985 and has been tested as Fla. 85-1.

ASEXUAL REPRODUCTION OF THE VARIETY

'Gulfbeauty' has been asexually propagated by budding onto Flordaguard peach rootstock in one experimental orchard at Gainesville for 3 generations, which shows that characteristics are uniformly transmitted through succeeding propagations.

SUMMARY OF THE VARIETY

This new and distinct variety of plum tree is large, vigorous, and semi spreading in growth. It has an estimated chilling requirement of 250 chill units, but appears to have a high heat requirement for breaking dormancy. 'Gulfbeauty' trees bloom before the earliest standard Japanese varieties at Gainesville, but with or after the earliest standard Japanese varieties in north Florida locations. Winter temperatures of 14F. in Florida have not damaged wood or flower and leaf buds. 'Gulfbeauty' is adapted to the winters of north central and north Florida, flowering with 'Gulfruby' (unpatented) plum and is cross pollinated by 'Gulfruby'.

'Gulfbeauty' is an efficient pollenzier for 'Gulfruby'. Neither 'Gulfbeauty' nor 'Gulfruby' are self fruitful. 'Gulfbeauty' is a regular and productive bearer of medium size, firm, clingstone fruit with good eating quality and a sour skin. The fruit is further characterized by having deep red skin, firm, light yellow flesh, hanging on the tree 10 days after maturity (shipping ripe) and ripening 7 to 10 days before 'Gulfruby'. Fruit set is very high and heavy fruit thinning may be required to prevent limb breakage and size fruit properly. The new variety is distinguished from 'Gulfruby' in smaller leaves and a higher degree of resistance in leaves, twigs, and fruit to bacterial leaf spot, (*Xanthomonas campestris*), and smaller, earlier ripening fruit. Fruit of 'Gulfbeauty' are highly resistant to sun scald ('Gulfruby' is highly susceptible), concentric skin cracks, and split stones. Leaves have moderate resistant to leaf scald (*Xylellia fastidiosa*).

BRIEF DESCRIPTION OF THE DRAWING

The drawing is a color photograph, showing a typical stem, and leaves and ripe fruit as viewed from the stem, the distal end, and side views perpendicular and parallel to the suture. The photograph colors are as nearly true as is reasonably possible in a color representation of this type.

DETAILED BOTANICAL DESCRIPTION

The following is a detailed botanical description of 'Gulfbeauty' plum tree, its flowers, foliage and fruit based on observations of specimens grown near Gainesville, Fla. on Flordaguard peach rootstock. Color names with a capital letter designate values based upon the Pantone Book of Color published in 1990 by Harry N. Abrams, Inc. N.Y.

Tree:

*Size.*—Large and in the upper range for a Japanese plum.

*Vigor.*—Vigorous and in the upper range for a Japanese plum.

*Form.*—Semi-spreading.

*Density.*—Medium dense in branching habit and in the middle range for a Japanese plum.

*Shape.*—Rounded.

*Productivity.*—Productive and requires fruit thinning to prevent limb breakage and size fruit when cross pollinated with suitable pollinizers.

*Bearing.*—Regular.

*Cold hardiness.*—Hardy under the coldest Florida temperatures (14F.).

*Chilling requirement.*—Estimated 250 chill units based on bloom time and fruitfullness following annually diverse winter chilling in Florida.

Trunk:

*Size.*—Medium as trunk diameter results from longer terminal growth at the expense to the tree diameter.

*Texture.*—Medium shaggy and in the middle range for a Japanese plum.

*Color.*—Chinchilla (Pantone 17-1109).

Branches:

*Size.*—Medium diameter as scaffold branches grow more at terminals at the expense to the branch diameter.

*Texture.*—Smooth.

*Lenticels.*—Medium number and in the middle range for Japanese plum. Size is 1 to 2 mm long and 0.2 to 0.3 mm width on second year old wood.

*Color.*—Aztec (Pantone 18-1130).

*Fruiting.*—Fruits on spurs and hanging branches (whips).

Leaves:

*Size.*—94 mm length, (including petiole), 41 mm wide.

*Form.*—Elliptical with acute tip and obtuse base.

*Margin.*—Double serrate.

*Thickness.*—Medium and in the middle range for a Japanese plum.

*Surface.*—Upper, reticulate; Lower, medium veined.

*Texture.*—Glabrous.

*Petiole.*—12 mm length, 2 mm diameter, and Grass Green (Pantone 15-6437).

*Glands.*—1 to 2 small globose glands on upper portion of petiole.

*Color.*—Upper, Forest Green (Pantone 17-0230); lower, Shamrock Green (Pantone 15- 6432).

Flower buds:

*Size.*—Small and slightly shorter than leaf bud at the node.

*Length.*—Medium, 2 mm length.

*Form.*—Plump and free.

*Color.*—Glaze Ginger (Pantone 18-1154).

Flowers:

*Blossom period.*—About 10 days.

*Size.*—Small to medium for the range in Japanese plums.

*Pollen.*—Abundant and yellow.

*Color.*—White.

*Date.*—Bloom ranging February 5 to 15 at Gainesville.

Fruit:

*Maturity date.*—May 5 to 8 at Gainesville.

*Weight.*—50 to 55 grams.

*Size.*—length 4.7 cm; width 4.7 cm.

*Form.*—Round.

*Suture.*—Slightly furrowed at stem end.

*Base.*—Nearly round, slightly flat.

*Apex.*—Round.

*Cavity.*—Circular at top to bottom. 3 mm depth; 10 mm wide at top; 1 mm wide at bottom.

*Stem.*—Medium at 3 to 5 mm length.

Flesh:

*Texture.*—Firm and fine.

*Fibers.*—Small and tender.

*Flavor or eating quality.*—Sweet flesh with tart skin and little bitterness.

*Juice.*—Juicy.

*Aroma.*—Lightly scented.

*Color.*—Cornsilk (Pantone 13-0936) to Lemon (Pantone 13-0752).

Skin:

*Thickness.*—Medium.

*Texture.*—Medium.

*Bloom* (*wax*).—Moderate.

*Color.*—Crimson (Pantone 19-1762) to Cardinal (Pantone 18-1643).

*Taste.*—Tart.

Stone:

*Type.*—Clingstone.

*Size.*—Length 2.0 cm. Width 1.6 cm.

*Form.*—Ovate.

*Base.*—Rounded.

*Apex.*—Acuminate.

*Sides.*—Equal.

*Surface.*—Small pits throughout.

*Ridges.*—Narrow on suture.

*Color.*—Alabaster (Pantone 12-0812).

Use: Market-local and long distance for fresh markets. The plum tree and its fruit herein described may vary slightly in detail due to climate, soil conditions, and cultural practices under which the variety may be grown.

I claim:

1. A new and distinct variety of plum tree, substantially as illustrated and described, which is vigorous, large, and semi spreading in growth and is adapted to central and north Florida producing annual crops of medium size, clingstone fruit with full red skin and pale yellow flesh, ripening a week before 'Gulfruby' and having firm flesh with good shipping characteristics for its intended fresh market use.

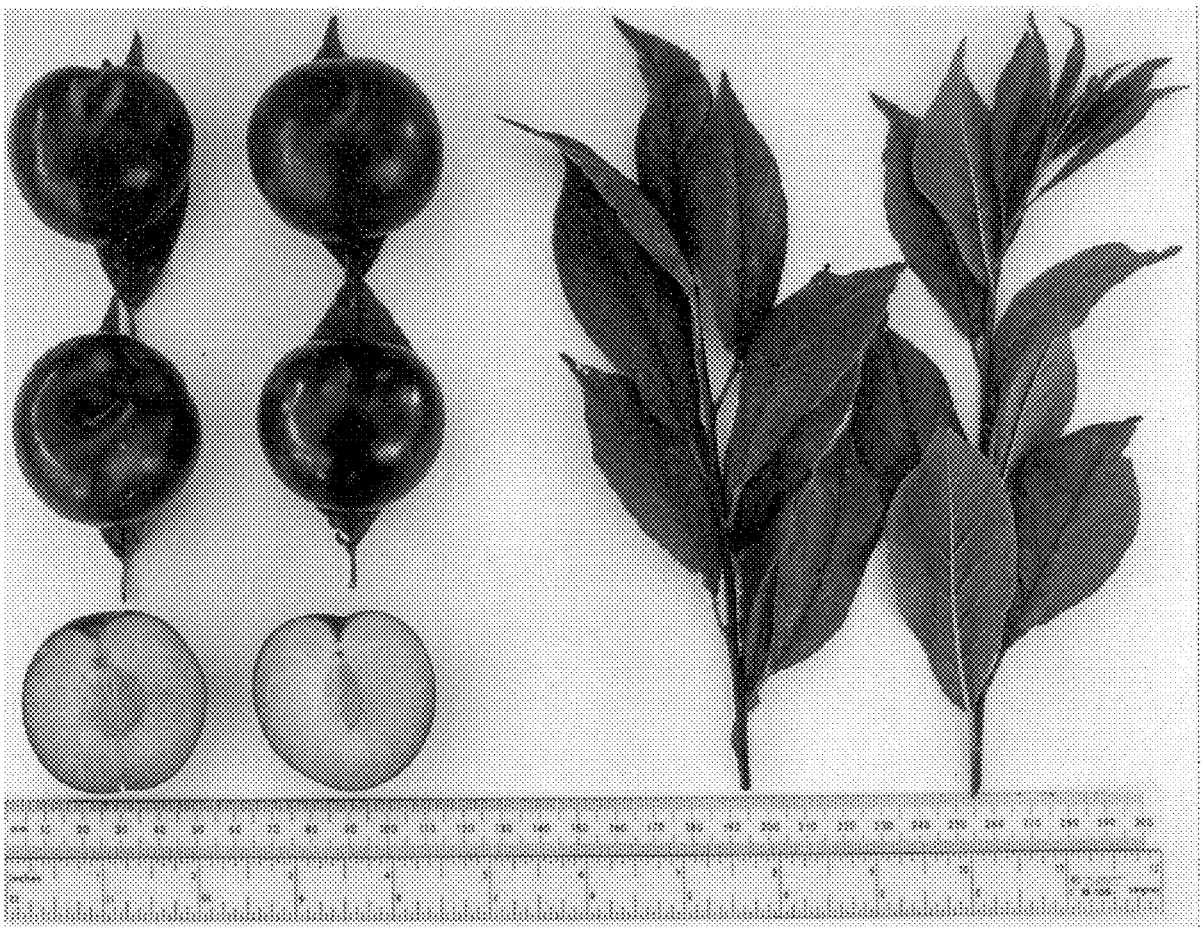

* * * * *